US012778535B2

(12) United States Patent
Niibe

(10) Patent No.: US 12,778,535 B2
(45) Date of Patent: Nov. 3, 2026

(54) RADIOGRAPHING CONTROL APPARATUS AND RADIOGRAPHING SYSTEM

(71) Applicant: CANON KABUSHIKI KAISHA, Tokyo (JP)

(72) Inventor: Yusuke Niibe, Kanagawa (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 103 days.

(21) Appl. No.: 19/011,321

(22) Filed: Jan. 6, 2025

(65) Prior Publication Data

US 2025/0228517 A1 Jul. 17, 2025

(30) Foreign Application Priority Data

Jan. 15, 2024 (JP) ................................ 2024-004201

(51) Int. Cl.
*A61B 6/00* (2024.01)
*A61B 6/04* (2006.01)
*A61B 6/58* (2024.01)

(52) U.S. Cl.
CPC ................ *A61B 6/547* (2013.01); *A61B 6/04* (2013.01); *A61B 6/589* (2013.01)

(58) Field of Classification Search
CPC ............ A61B 6/04; A61B 6/547; A61B 6/589
See application file for complete search history.

(56) References Cited

U.S. PATENT DOCUMENTS

2003/0016785 A1* 1/2003 Motoki .............. H04N 1/32561 378/98
2003/0219101 A1* 11/2003 Tsujii .................. A61B 6/4429 378/205
2008/0154744 A1* 6/2008 Amitani .................. A61B 6/00 705/26.1
2009/0272907 A1* 11/2009 Hara .................... A61B 6/0414 250/370.09
2010/0008465 A1* 1/2010 Matsuura ............... A61B 6/032 378/92
2012/0029344 A1* 2/2012 Nakayama ............. A61B 6/022 378/62
2012/0051521 A1* 3/2012 Nishino ............... A61B 6/4405 378/98.5
2012/0219119 A1* 8/2012 Arima .................... A61B 6/461 378/165
2012/0321034 A1* 12/2012 Nakayama ............. A61B 6/022 378/62

(Continued)

FOREIGN PATENT DOCUMENTS

JP 2020199163 A 12/2020

*Primary Examiner* — Blake C Riddick
(74) *Attorney, Agent, or Firm* — Canon U.S.A., Inc. IP Division

(57) ABSTRACT

A radiographing control apparatus includes a first acquisition unit for acquiring an optical image regarding a subject, an estimation unit for estimating information regarding a part of the subject from the optical image, a second acquisition unit for acquiring part-to-be-imaged information in an imaging protocol regarding the subject, and a determination unit for determining whether there is consistency between the information regarding the part estimated by the estimation unit and the part-to-be-imaged information acquired by the second acquisition unit based on similarity.

8 Claims, 10 Drawing Sheets

(56) References Cited

U.S. PATENT DOCUMENTS

| | | | | |
|---|---|---|---|---|
| 2013/0058557 | A1* | 3/2013 | Nagatsuka | A61B 5/08 382/132 |
| 2013/0251232 | A1* | 9/2013 | Koishi | G16H 20/40 382/132 |
| 2013/0274585 | A1* | 10/2013 | Wanda | A61B 5/0095 600/407 |
| 2015/0272703 | A1* | 10/2015 | Arima | A61B 6/461 378/62 |
| 2016/0277648 | A1* | 9/2016 | Yamaguchi | G06V 10/141 |
| 2017/0020470 | A1* | 1/2017 | Tezuka | A61B 6/4233 |
| 2017/0172535 | A1* | 6/2017 | Kim | A61B 6/032 |
| 2017/0281113 | A1* | 10/2017 | Tanaka | A61B 6/40 |
| 2018/0333128 | A1* | 11/2018 | Obara | A61B 6/4291 |
| 2019/0046128 | A1* | 2/2019 | Yamazaki | A61B 5/0082 |
| 2020/0305821 | A1* | 10/2020 | Sendai | A61B 6/025 |
| 2021/0350532 | A1* | 11/2021 | Kimmel | A61B 5/0035 |
| 2021/0369229 | A1* | 12/2021 | Okumura | A61B 6/468 |
| 2022/0287672 | A1* | 9/2022 | Matsuura | A61B 6/4417 |
| 2023/0225692 | A1* | 7/2023 | Okutani | A61B 6/04 378/64 |
| 2023/0252635 | A1* | 8/2023 | Hasegawa | A61B 6/54 382/128 |
| 2023/0270334 | A1* | 8/2023 | Horiuchi | A61B 5/0064 600/476 |
| 2025/0095194 | A1* | 3/2025 | Ito | A61B 6/545 |
| 2025/0107768 | A1* | 4/2025 | Ito | A61B 6/032 |
| 2025/0302418 | A1* | 10/2025 | Sugahara | A61B 6/4405 |
| 2025/0384582 | A1* | 12/2025 | Sugahara | G06T 7/74 |

* cited by examiner

FIG.9

10900

| DETERMINATION RESULT | CONSISTENCY BETWEEN PARTS | NOTIFICATION ABOUT DETECTION RESULT |
|---|---|---|
| NOT TARGET | — | SET INSPECTION INFORMATION |
| HUMAN BODY HAS YET TO BE DETECTED | — | UNABLE TO DETECT HUMAN BODY |
| PARTS ARE INCONSISTENT WITH EACH OTHER | — | CHECK PART TO BE IMAGED |
| DIRECTIONS ARE INCONSISTENT WITH EACH OTHER | STRICTLY CONSISTENT WITH EACH OTHER | CHECK IMAGING DIRECTION |
| DIRECTIONS ARE INCONSISTENT WITH EACH OTHER | SIMILAR PARTS ARE CONSISTENT WITH EACH OTHER | SIMILAR PARTS. CHECK IMAGING DIRECTION |
| LITERALITIES ARE INCONSISTENT WITH EACH OTHER | STRICTLY CONSISTENT WITH EACH OTHER | CHECK LEFT AND RIGHT SIDES OF SUBJECT TO BE IMAGED |
| LITERALITIES ARE INCONSISTENT WITH EACH OTHER | SIMILAR PARTS ARE CONSISTENT WITH EACH OTHER | SIMILAR PARTS. CHECK LEFT AND RIGHT SIDES OF SUBJECT TO BE IMAGED |
| CONSISTENT | STRICTLY CONSISTENT WITH EACH OTHER | NORMAL POSITION |
| CONSISTENT | SIMILAR PARTS ARE CONSISTENT WITH EACH OTHER | SIMILAR PARTS. NORMAL POSITION |
| UNABLE TO DETERMINE | — | ERROR |

RADIOGRAPHING CONTROL APPARATUS AND RADIOGRAPHING SYSTEM

BACKGROUND OF THE DISCLOSURE

Field of the Disclosure

The present disclosure relates to a radiographing control apparatus and a radiographing system.

Description of the Related Art

Radiation imaging apparatus using a flat panel detector (FPD) formed of a semiconductor material has been widely used as an imaging apparatus used for medical image diagnosis or non-destructive inspection using radiation. For example, in medical image diagnosis, such a radiation imaging apparatus is used as a digital imaging apparatus that performs still-image capturing such as general imaging and moving-image capturing such as fluoroscopy.

In radiographic imaging, registration of a subject is performed as a previous step of imaging. There are confirmed cases where an image loss occurs due to inappropriate registration. In recent years, a radiographic imaging system (radiographing system) including an optical camera capable of checking a state of a subject (optical imaging apparatus) as a configuration for assisting the registration.

Japanese Patent Application Laid-Open No. 2020-199163 discusses a technique of analyzing a subject image acquired by an optical imaging apparatus at the time of radiographic imaging, and displaying an analysis result on a display apparatus to notify an operator of the analysis result.

In the technique discussed in Japanese Patent Application Laid-Open No. 2020-199163, there is a room for improvement regarding an analysis method and a method of notifying an analysis result.

SUMMARY OF THE DISCLOSURE

According to an aspect of the present disclosure, a radiographing control apparatus includes a first acquisition unit for acquiring an optical image regarding a subject, an estimation unit for estimating information regarding a part of the subject from the optical image, a second acquisition unit for acquiring part-to-be-imaged information in an imaging protocol regarding the subject, and a determination unit for determining whether there is consistency between the information regarding the part estimated by the estimation unit and the part-to-be-imaged information acquired by the second acquisition unit based on similarity.

Further features of the present disclosure will become apparent from the following description of exemplary embodiments with reference to the attached drawings.

BRIEF DESCRIPTION OF THE DRAWINGS

FIG. 9 is a table indicating correspondence between a determination result based on image analysis and notification about a determination result.

DESCRIPTION OF THE EMBODIMENTS

An exemplary embodiment of the present disclosure will now be described in detail with reference to the drawings. The present disclosure is not limited to configurations described in the exemplary embodiment. Modification, such as replacement of part of each configuration or part of processing with equivalents and omission of part of each configuration or part of processing, may be made within a scope in which a similar effect can be obtained.

[Radiographing System]

Figure 1:
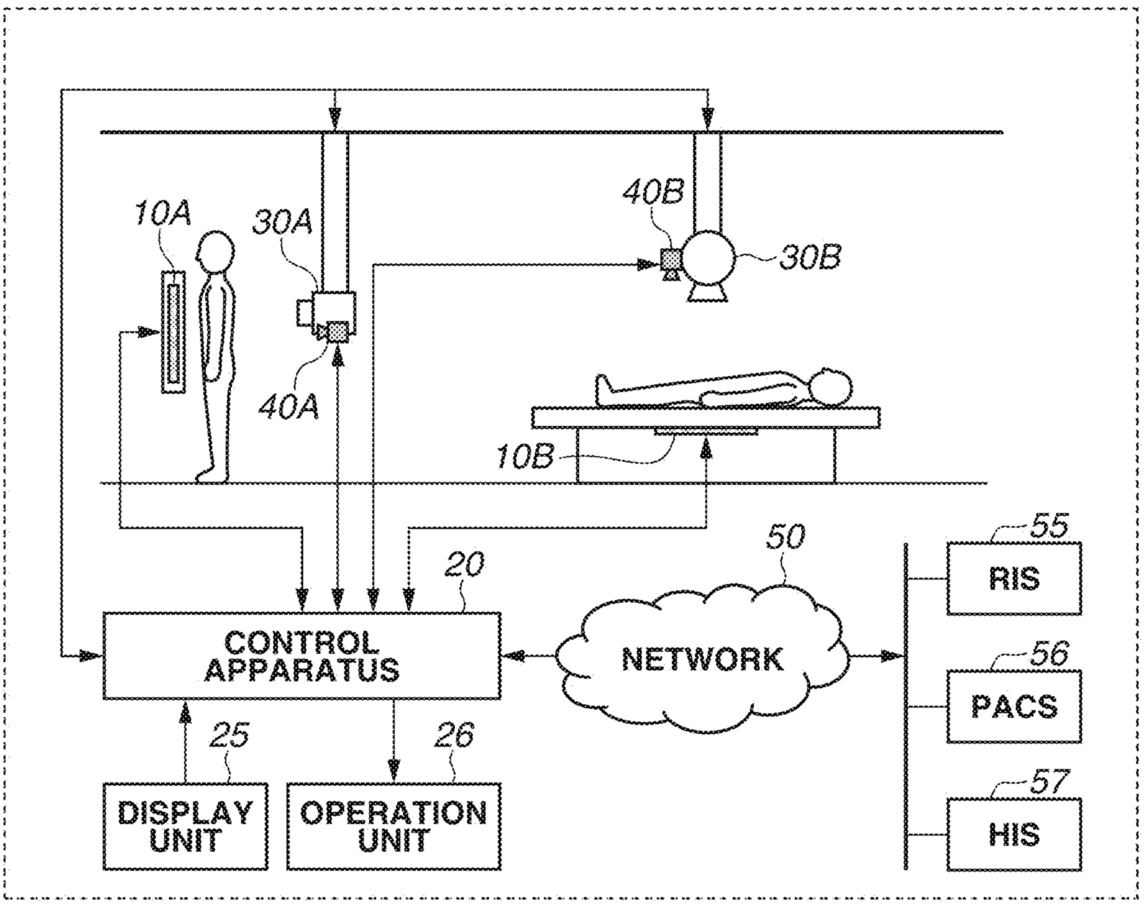
FIG. 1 is a diagram illustrating an overall configuration of radiation imaging.

FIG. 1 is an overall view illustrating an environment in which a radiation detection apparatus 10 (a radiographing apparatus or a radiation imaging apparatus) is utilized, and illustrates the radiation detection apparatus 10 (10A and 10B) and a control apparatus 20 serving as a radiation control apparatus. The radiation detection apparatus 10 and the control apparatus 20 constitute a radiographing system to be described below. The radiation imaging apparatus will be described below as a control apparatus in a simplified manner. FIG. 1 further illustrates a radiation generating apparatus 30 (30A and 30B), an optical imaging apparatus 40 (40A and 40B), a display unit 25, an operation unit 26, a radiology information system (RIS) 55, a picture archiving and communication system (PACS) 56, and a hospital information system (HIS) 57.

The control apparatus 20 is an apparatus that relays the radiation detection apparatus 10, the radiation generating apparatus 30, and various apparatuses that are connectable via a network 50, and performs various kinds of control. Details of the control apparatus 20 will be described below.

The radiation generating apparatus 30 (radiation irradiation apparatus) includes a radiation tube that generates radiation, and irradiates a subject, such as a patient, with radiation. Assume that radiation mentioned herein also includes an α-ray, a β-ray, a γ-ray, a particle ray, and a cosmic ray as well as an X-ray. Assume that the radiation generating apparatuses 30A and 30B are appropriately selected and used depending on contents of imaging.

The radiation generating apparatuses 30A and 30B are collectively referred to as the radiation generating apparatus 30 when there is no specific preference.

The radiation detection apparatus 10 (radiographing apparatus, radiation imaging apparatus) is an apparatus that generates an image based on radiation emitted from the radiation generating apparatus 30. The radiation detection apparatus 10 is, for example, a flat-panel detector. Assume that the radiation detection apparatuses 10A and 10B are appropriately selected and used depending on contents of imaging. The radiation detection apparatuses 10A and 10B are collectively referred to as the radiation detection apparatus 10 when there is no specific preference.

The radiation detection apparatus 10 detects radiation that has been emitted from the radiation generating apparatus 30 and has penetrated an examinee, and outputs image data corresponding to radiation. The image data can also be referred to as a medical image or a radiation image. Specifically, the radiation detection apparatus 10 detects radiation that has penetrated the examinee as a charge corresponding to a penetrating radiation dose. For example, a direct conversion type sensor or an indirect type sensor is used in the radiation detection apparatus 10. The direct conversion type sensor, such as an amorphous selenium (a-Se) sensor, directly converts radiation into a charge. The indirect type sensor uses a scintillator, such as a cesium iodide (CsI) scintillator, and a photoelectric conversion element, such as an amorphous silicon (a-Si) element, that convert radiation into visual light. The radiation detection apparatus 10 also performs analog/digital (A/D) conversion on the detected charge to generate image data, and outputs the image data to the control apparatus 20.

The optical imaging apparatus 40 is a camera apparatus for capturing an image of a state of a subject serving as the examinee that undergoes radiographic imaging. Assume that the optical imaging apparatuses 40A and 40B are appropriately selected and used depending on contents of imaging. The optical imaging apparatuses 40A and 40B are collectively referred to as the optical imaging apparatus 40 when there is no specific preference.

The display unit 25 is, for example, a display apparatus including a monitor such as a liquid crystal display. The display unit 25 also includes an operation unit (not illustrated). The operation unit 26 is an input device including a keyboard, a pointing device (e.g., a mouse), and a touch panel.

The RIS 55, the PACS 56, and the HIS 57 are services that cooperate with the control apparatus 20 via the network 50 and extend various kinds of functions regarding radiographic imaging. The control apparatus 20 is connected to the RIS 55, the PACS 56, and the HIS 57 via the network 50, and is capable of communicating a radiation image, patient information, and the like. While the description has been given assuming that the RIS 55, the PACS 56, and the HIS 57 are included in a radiographing system 1, the radiographing system 1 may not include at least part of the RIS 55, the PACS 56, and the HIS 57.

The control apparatus 20 controls radiographic imaging using the radiation detection apparatus 10 and the radiation generating apparatus 30.

Figure 4:
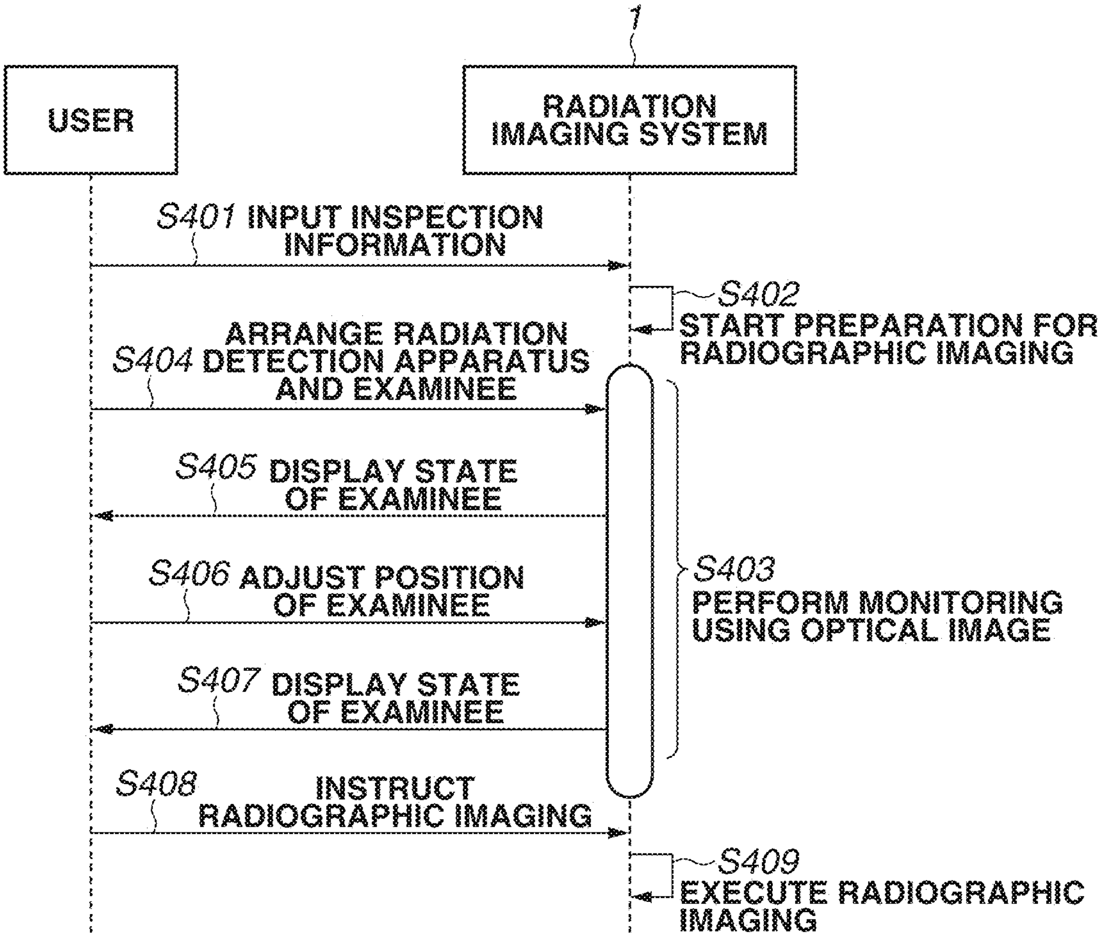
FIG. 4 is a diagram illustrating a utilization sequence of the radiographing system.

The radiation imaging apparatus according to the present exemplary embodiment is used in, for example, a sequence illustrated in FIG. 4.

In step S401, a user (radiology technician) using the radiographing system 1 inputs inspection information to the radiographing system 1.

In step S402, the radiographing system 1 starts preparation for radiographic imaging.

In step S403, the radiographing system 1 monitors the subject serving as the examinee with optic imaging as one of the preparation for radiographic imaging.

In step S404, the user arranges the radiation detection apparatus 10 and the examinee.

In step S405, the user checks the state of the examinee displayed on the radiographing system 1.

In step S406, the user adjusts the position of the radiation detection apparatus 10 and the position of the examinee if a positional relationship between the radiation detection apparatus 10 and the examinee is inappropriate.

In step S407, the user checks the state of the examinee displayed on the radiographing system 1.

In step S408, the user checks whether the positional relationship between the radiation detection apparatus 10 and the examinee is appropriate, and gives an instruction for radiographic imaging to the radiographing system 1.

In step S409, the radiographing system 1 executes radiographic imaging.

[Control Apparatus]

Figure 3:
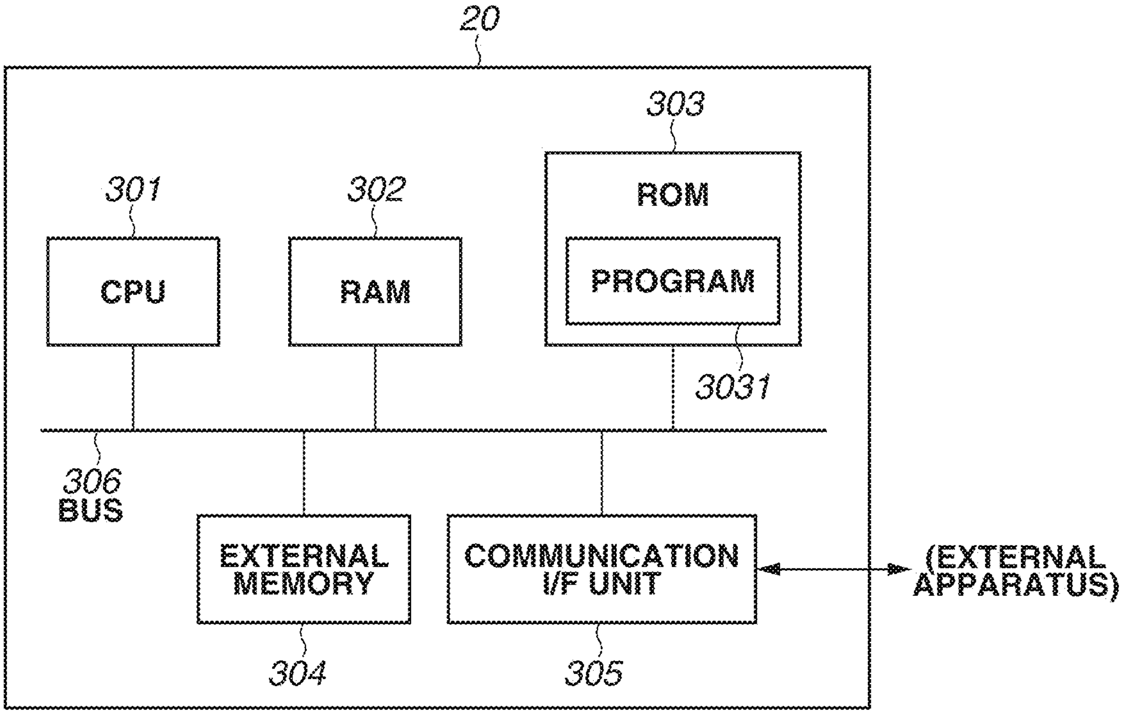
FIG. 3 is a diagram illustrating a hardware configuration of the radiographing control apparatus.

FIG. 3 is a diagram illustrating a configuration of the control apparatus 20. The control apparatus 20 includes a central processing unit (CPU) 301, a random-access memory (RAM) 302, a read-only memory (ROM) 303, an external memory 304, a communication interface (I/F) unit 305, and a bus 306. The CPU 301, the RAM 302, the ROM 303, the external memory 304, and the communication I/F unit 305 are communicably connected to each other via the bus 306.

The CPU 301 performs integrated control of operations of the control apparatus 20, and performs control of each component illustrated in FIG. 3 via the bus 306.

The RAM 302 (rewritable memory) functions as a main memory and work area of the CPU 301, and the like. The CPU 301 loads a computer program 3031, data, or the like from the ROM 303 into the RAM 302, and executes the computer program 3031 to implement various kinds of functional operations. The control apparatus 20 has an application function that operates on a computer. That is, the control apparatus 20 including one or more processors and memories implements each functional unit described below by executing the program stored in the memories with the processors. However, part or all of the functional units may be implemented by dedicated hardware.

The ROM 303 stores the computer program 3031, data, and the like that are used for execution of processing by the CPU 301. The computer program 3031, data, and the like may be stored in the external memory 304.

The external memory 304 is a high-capacity storage, and is implemented by, for example, a hard disk device, an integrated circuit (IC) memory, or the like. The external memory 304 stores, for example, various kinds of data, various kinds of information, and the like that are used for execution of the computer program 3031 or the like to perform processing by the CPU 301. The external memory 304 also stores, for example, various kinds of data, various kinds of information, and the like that are obtained by the CPU 301 executing the computer program 3031 or the like to perform processing.

The communication I/F unit 305 is in charge of communication between the control apparatus 20 and the outside. The control apparatus 20 is connected to the radiation generating apparatus 30, the radiation detection apparatus 10, and the optical imaging apparatus 40 using a wired or wireless network or a dedicated line via the communication I/F unit 305.

The bus 306 is used for communicably connecting the CPU 301, the RAM 302, the ROM 303, the external memory 304, and the communication I/F unit 305.

Figure 2:
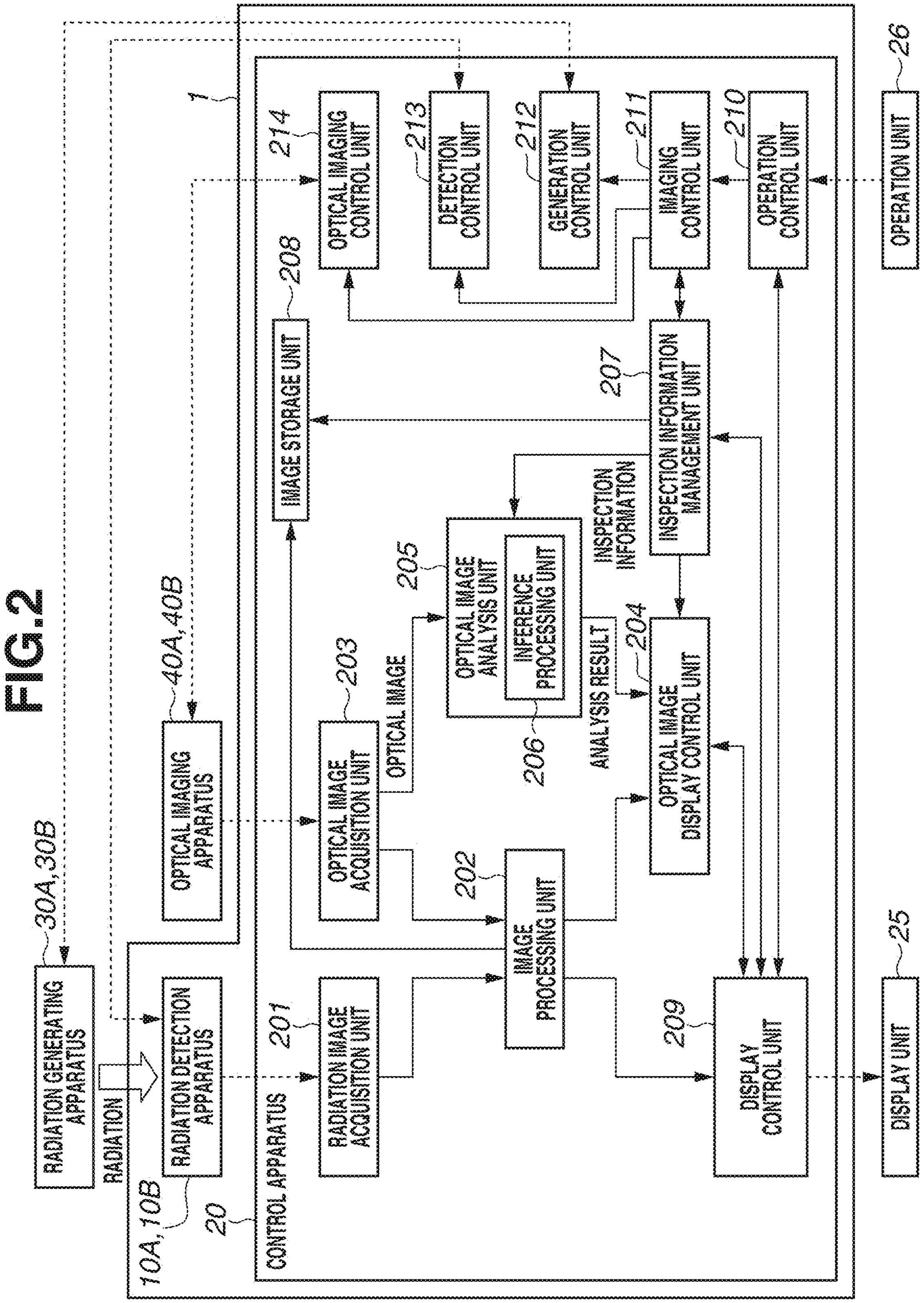
FIG. 2 is a functional block diagram illustrating a radiographing system and a radiographing control apparatus.

Next, details (functional blocks) of the radiographing system 1 and the control apparatus 20 serving as the radiographing control apparatus will be described with reference to FIG. 2. The radiographing system 1 includes the radiation detection apparatus 10 and the control apparatus 20 serving as the radiographing control apparatus. The control apparatus 20 will be described in detail below.

An imaging control unit 211 of the control apparatus 20 controls a generation control unit 212, a detection control unit 213, and an optical imaging control unit 214 based on an instruction from an operation control unit 210 and inspection information managed by an inspection information management unit 207. The inspection information includes information regarding a dose, an irradiation time (ms), a tube current (mA), a tube voltage (kV), and a lighting field serving as a region in which radiation is detected. These pieces of information are transmitted to the radiation detection apparatus 10 via the imaging control unit 211 and the detection control unit 213.

The generation control unit 212 controls timings at which the radiation generating apparatus 30 generates radiation and an imaging condition of the radiation.

The generation control unit 212 outputs information, such as an irradiation control signal, to the radiation generating apparatus 30 based on radiation dose information or the like. The irradiation control signal transmitted from the generation control unit 212 to the radiation generating apparatus 30 can include two signals of a stop signal (irradiation stop signal) and an irradiation signal (non-irradiation stop signal). The stop signal is for stopping irradiation with radiation. The irradiation signal is for performing irradiation with radiation. The generation control unit 212 controls output of both or either one of the stop signal and the irradiation signal, and can thereby control irradiation and stop of radiation from the radiation generating apparatus 30.

The detection control unit 213 communicates with the radiation detection apparatus 10 to perform various kinds of control for radiation imaging (radiographic imaging). The detection control unit 213 executes, for example, various kinds of communication processing associated with radiation, on the radiation detection apparatus 10. In this communication processing, pieces of information are communicated, such as setting information regarding an imaging condition, setting information regarding operation control, image information, and reached dose information.

The optical imaging control unit 214 controls the start and end of imaging performed by the optical imaging apparatus 40, a condition for acquiring an optical image, a timing, a frame rate, and functions such as zooming and focusing.

A radiation image acquisition unit 201 receives image data from the radiation detection apparatus 10. An image processing unit 202 performs image processing on the received image data as necessary, and provides the image data to a display control unit 209 or an image storage unit 208.

The display control unit 209 provides screen information regarding an imaging management application to the display unit 25.

A graphical user interface of the imaging management application displayed on the display unit 25 is operated in conjunction with an operation on the operation unit 26. It is thereby possible to perform input of information regarding the imaging management application via the operation unit 26. For example, in a case where a plurality of pieces of inspection information is displayed in a list format on the display unit 25, the operation unit 26 is capable of performing input operation to select one piece of inspection information from the list. The selected inspection information can be set as an inspection target. Alternatively, the user may directly input inspection information from the operation unit 26. The inspection information input in the imaging management application is managed by the inspection information management unit 207. A method of acquiring and setting the inspection information is not limited to the above-mentioned method. For example, the inspection information management unit 207 may directly acquire inspection information (e.g., an imaging protocol) set in an external apparatus. Thus, the inspection information management unit 207 may be referred to as an acquisition unit that acquires part-to-be-imaged information in the imaging protocol. When the inspection information management unit 207 is referred to as the acquisition unit, it is referred to as a second acquisition unit to be distinguished from an optical image acquisition unit 203 serving as a first acquisition unit that acquires an optical image.

The optical image acquisition unit 203 acquires an optical image from the optical imaging apparatus 40, and provides the optical image to the image processing unit 202 and an optical image analysis unit 205. The optical image acquisition unit 203 may be referred to as the first acquisition unit. The optical image is preferably moving images, but may be a still image that has been acquired on a sporadic basis. The image processing unit 202 performs image processing on the received optical image as appropriate, and provides the optical image to an optical image display control unit 204 or the image storage unit 208.

The optical image analysis unit 205 uses the optical image acquired from the optical image acquisition unit 203 and the inspection information acquired from the inspection information management unit 207 to perform the determination. The inspection information is specifically information regarding the imaging protocol, and more specifically, the part-to-be-imaged information. More specifically, the optical image analysis unit 205 analyzes the position, type, and orientation of a human body part of the subject within the optical image to determine whether they are consistent with setting content of the inspection information (the part-to-be-imaged information in the imaging protocol). At this time, the optical image analysis unit 205 performs determination about consistency between the subject's part information obtained by analysis of the optical image and the part-to-be-imaged information in the imaging protocol serving as the inspection information based on similarity between the pieces of information. Details of the determination will be described below. In the present exemplary embodiment, the optical image analysis unit 205 uses an inference processing unit 206 using machine learning to perform the determination, but may perform the determination using another method. In the following description, the optical image analysis unit 205 may be simply referred to as a determination unit. Similarly, the inference processing unit 206 may be simply referred to as an inference unit.

The optical image display control unit 204 performs display control regarding an image obtained by the optical imaging apparatus 40. For example, the optical image display control unit 204 processes the optical image and adds information to the optical image, and provides the optical image as image information to the display control unit 209. The image information provided to the display control unit 209 is utilized as part of information to be displayed on the graphical user interface of the imaging management application, and is displayed on the display unit 25.

In FIG. 1, the control apparatus 20 is described as one control apparatus for simplifying explanation, but may be composed of a plurality of apparatuses. For example, the optical imaging control unit 214, the detection control unit 213, the generation control unit 212, and the display control unit 209 may be independent apparatuses. Alternatively, the control apparatus 20 may be a combination of control apparatuses that are selectively provided with a plurality of functions of the optical imaging control unit 214, the detection control unit 213, the generation control unit 212, and the display control unit 209.

[Display of Optical Image]

Figure 5:
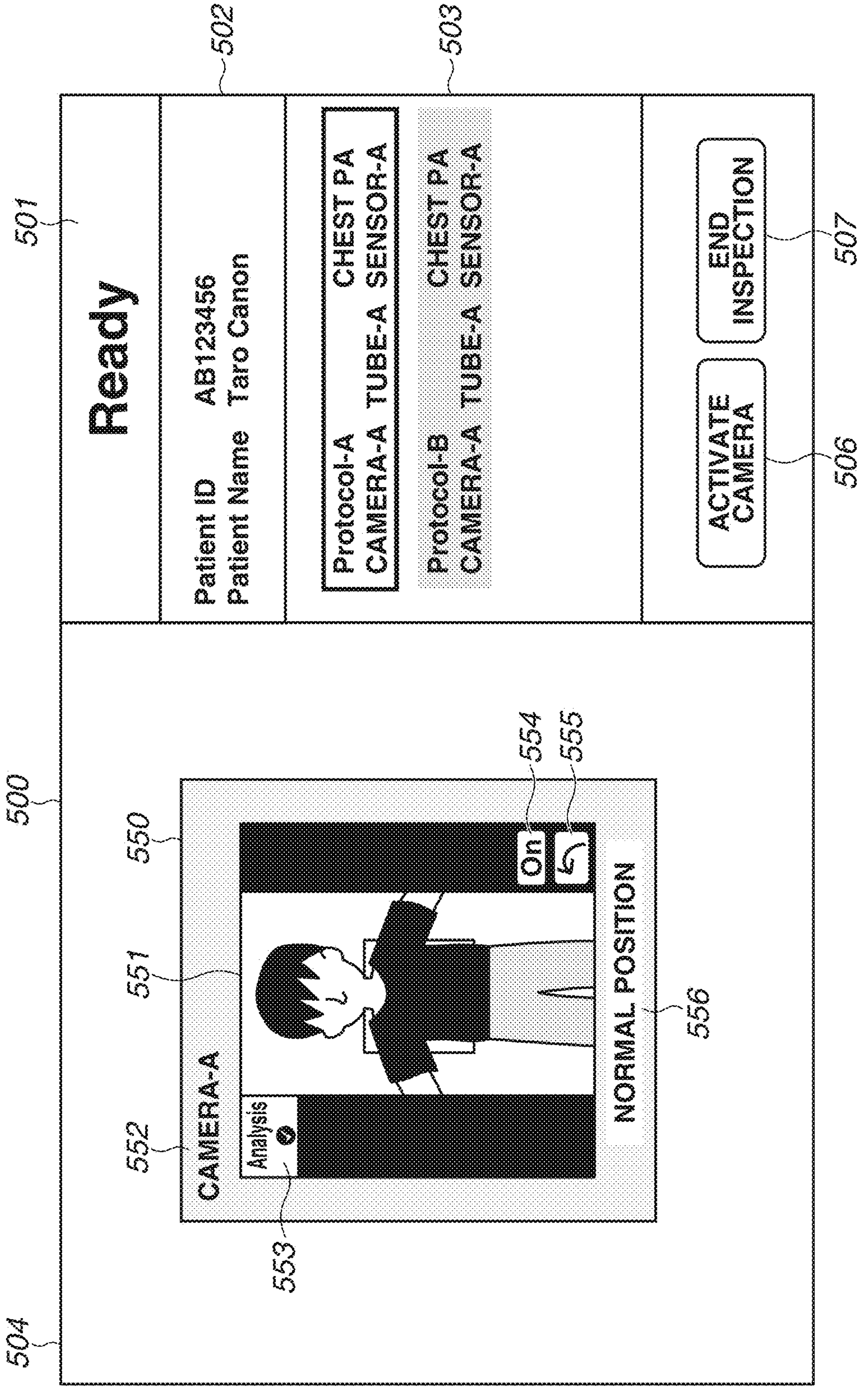
FIG. 5 is a diagram illustrating a display example of an optical image in a imaging management application.

Next, display of the optical image will be described with reference to FIG. 5. FIG. 5 is a diagram illustrating a display example of the optical image in the imaging management application.

In the present exemplary embodiment, an image of the state of the examinee at the time of radiographic imaging is captured by the optical imaging apparatus 40, and the obtained optical image is used for monitoring the state.

At the start of inspection in radiographic imaging, a screen 500 is displayed on a graphical user interface (GUI) of the imaging management application.

The screen 500 includes a radiographic imaging state 501, examinee information 502, inspection information 503, a radiation image display region 504, an optical image window 550, an optical image window display change button 506, and an inspection end button 507.

The radiographic imaging state 501 is information indicating whether the radiographic imaging can be started. In the present exemplary embodiment, radiographic imaging is started by pressing of an imaging start button (not illustrated), but the radiographic imaging state 501 may also serve as the radiographic imaging start button. The examinee information 502 is information indicating the examinee serving as a target of radiographic imaging.

The inspection information 503 is information regarding contents of imaging in the inspection and a thumbnail radiation image (reduced image) acquired by the radiation image acquisition unit 201. The user can select one content of imaging from contents of imaging listed in the inspection information 503, and prepare for next imaging. The screen 500 is in a state where a content of imaging in "Protocol-A" is selected.

The radiation image display region 504 is a region in which a radiographic image acquired by the radiation image acquisition unit 201 in the inspection is displayed. Since no image has been captured in a phase of displaying the screen 500, the radiation image display region 504 has no radiation image and is in blank. Information regarding imaging time and date regarding the radiographic imaging may be displayed so as to be superimposed on four corners of the radiation image display region 504 as a character string in a free layout.

The optical image window display change button 506 is a selection object that allows for manual change of display/non-display of the optical image window 550 by being pressed.

The inspection end button 507 is a selection object that allows for ending the inspection by being pressed.

The optical image window 550 displays the optical image acquired by the optical image acquisition unit 203, an analysis result of analysis performed by the optical image analysis unit 205, a button for controlling the optical image, and the like. On the optical image window 550, analysis for "Protocol-A", which is the content of imaging and being selected, is performed. The optical image window 550 is displayed so as to be superimposed on the radiation image display region 504.

The optical image window 550 includes an optical image display region 551, camera information 552, an optical-image-analysis-being-executed icon 553, an optical image display change button 554, an optical image rotation button 555, and an optical image analysis result 556.

The optical image acquired by the optical image acquisition unit 203 is displayed in the optical image display region 551. Image processing has not been performed on the optical image in FIG. 5, but may be performed to make the optical image easily viewable by the user.

Information regarding the optical imaging apparatus 40 is displayed in the camera information 552.

The optical-image-analysis-being-executed icon 553 is information indicating whether image analysis is being executed by the optical image analysis unit 205. For example, in a case where the optical image analysis processing is being executed, the optical-image-analysis-being-executed icon 553 is displayed so as to visually notify the user that the optical image analysis is being executed. In a case where the optical image analysis processing is not being executed, the optical-image-analysis-being-executed icon 553 may be hidden or grayed out.

The optical image display change button 554 is a selection object that allows for manual change of display/non-display of the optical image in the optical image display region 551.

The optical image rotation button 555 is a selection object that allows for rotation of the optical image in the optical image display region 551. In the present exemplary embodiment, there is only left rotation, but right rotation may be added or a format of selecting a rotation angle may be adopted.

The optical image analysis result 556 is a message region (notification region) in which a result of image analysis performed by the optical image analysis unit 205 is displayed.

[Notification About Analysis Result]

Figure 6A:
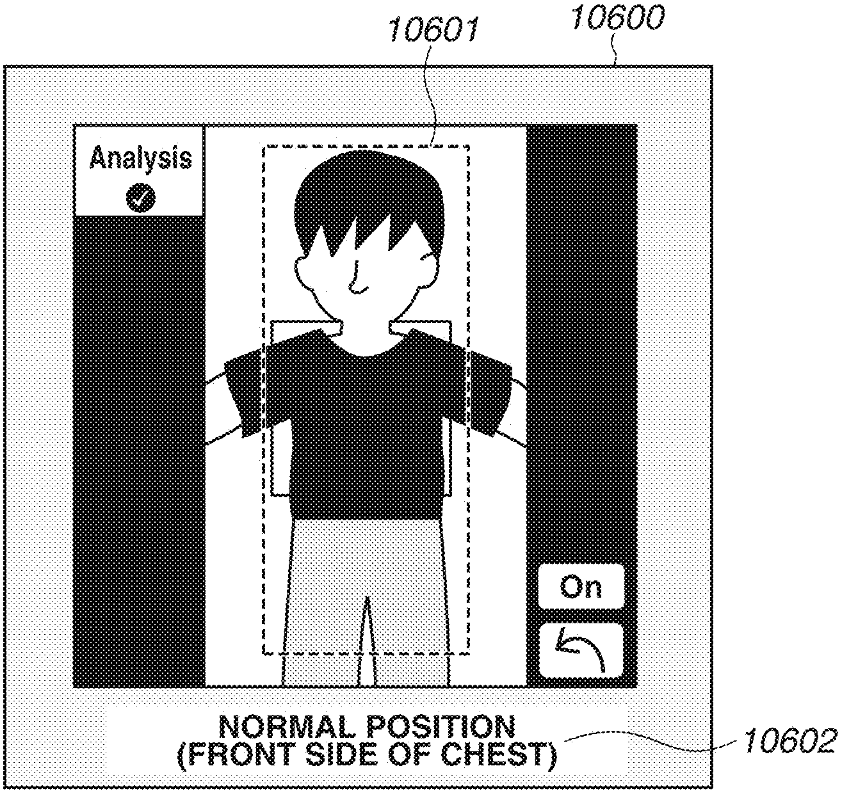
FIGS. 6A and 6B are diagrams each illustrating an example of notification about an analysis result in the imaging management application.
Figure 6B:
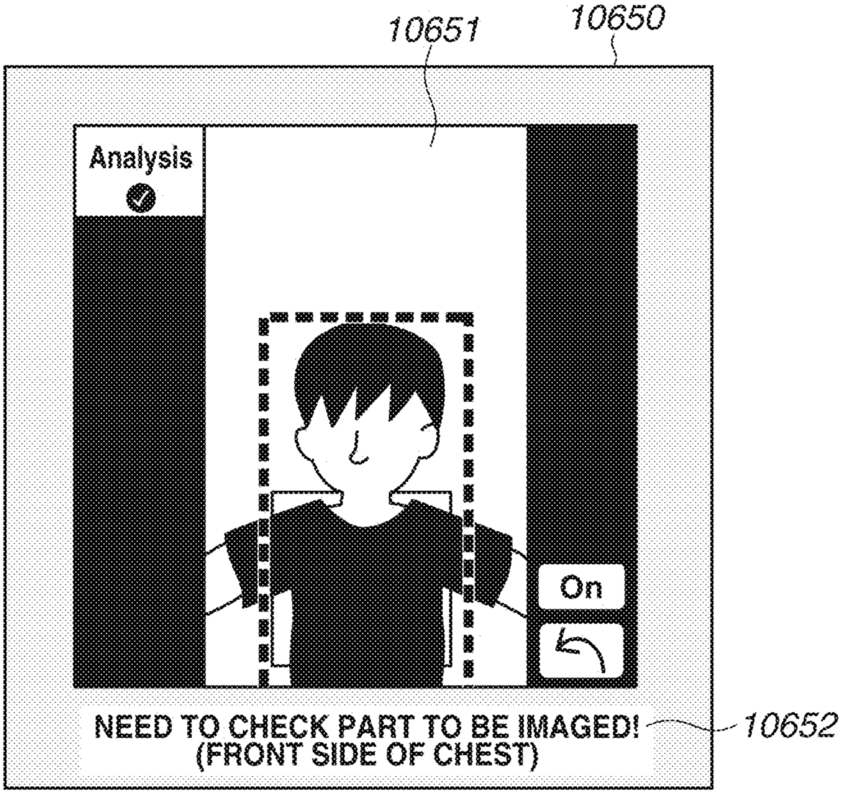

Subsequently, details of notification of a analysis result will be described with reference to FIGS. 6A and 6B. FIG. 6A is a diagram illustrating a notification example 1 regarding an analysis result in the imaging management application. FIG. 6B is a diagram illustrating a notification example 2 regarding an analysis result in the imaging management application.

In a case where the optical image analysis is performed, first, an optical image analysis target detection frame 10601 is displayed in a screen state 10600 of the above-mentioned optical image window 550. The optical image analysis target detection frame 10601 is a frame indicating the optical image analysis unit 205 having succeeded in detecting a single human body and its detection region. For example, the optical image analysis target detection frame 10601 is hidden in a case where the optical image analysis unit 205 has yet to detect the human body, and displays the optical image analysis target detection frame 10601 in a case where the optical image analysis unit 205 has detected the human body. This enables visual notification about the result of detection of the human body in the optical image analysis and its region to the user. In a case where the human body is detected in an abnormal position, an optical image analysis target detection frame 10651 may be displayed in a highlighted manner as illustrated in a screen state 10650 of the above-mentioned optical image window 550. That is, how to display an optical image analysis target detection frame may be changed depending on a detection state of the human body.

In the screen state 10600, notification 10602 is also given as the optical image analysis result 556. The notification 10602 is notification given in a case where the human body is normally detected corresponding to the inspection information. As the notification 10602, notification indicating "NORMAL POSITION" is given and information indicating "FRONT SIDE OF CHEST" as the current content of imaging is displayed. With this notification, it is possible to grasp that the human body is in a normal position with respect to the content of imaging to be scheduled.

In a screen state 10605, in contrast, notification 10652 is given as the optical image analysis result 556. The notification 10652 is notification to be given in a case where the human body is detected in an abnormal position not corresponding to the inspection information. As the notification 10652, notification indicating "NEED TO CHECK PART TO BE IMAGED!" is given and information indicating "FRONT SIDE OF CHEST" serving as the current content of imaging is displayed. With this notification, it is possible to grasp that the human body is in an abnormal position with respect to the content of imaging to be scheduled.

[Inspection Processing]

Figure 7:
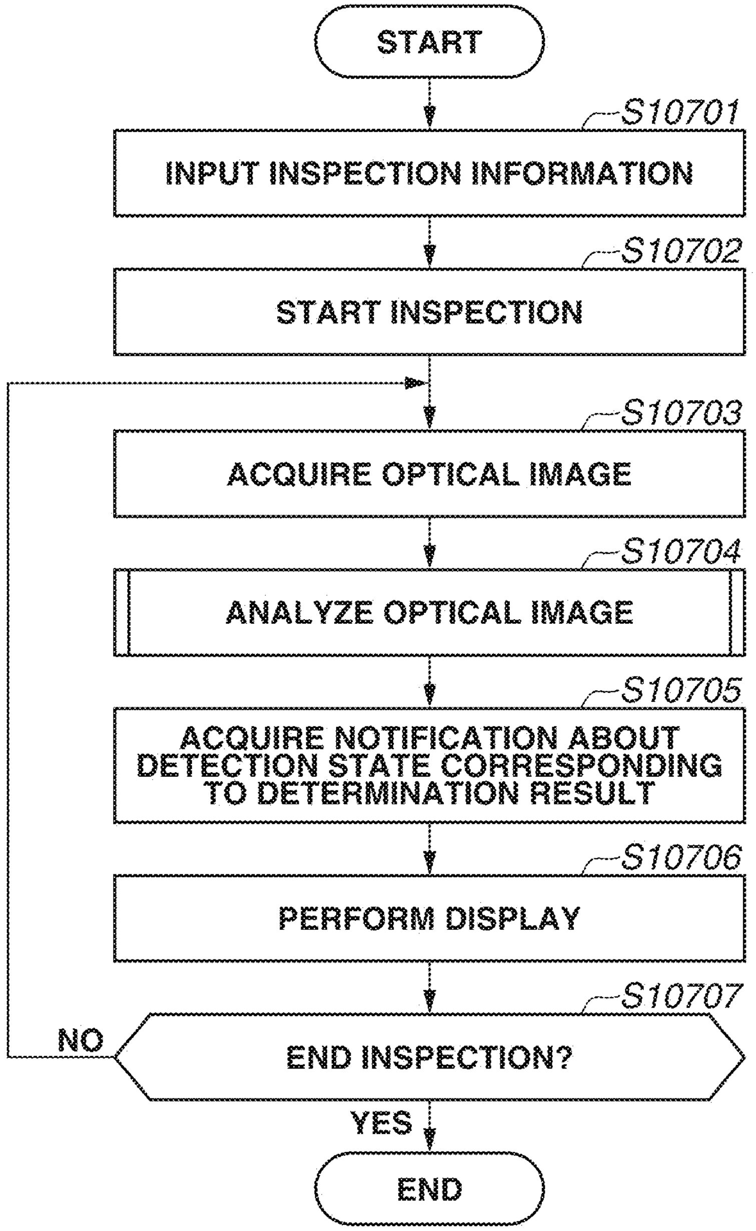
FIG. 7 is a flowchart illustrating inspection processing.

Next, inspection processing will be described with reference to FIG. 7. FIG. 7 is a flowchart of the inspection processing. Control corresponding to this flowchart is executed by the control apparatus 20. Specifically, the control is implemented by the CPU 301 included in the control apparatus 20 loading the computer program 3031 stored in the ROM 303 or the like in the RAM 302 and operating as a corresponding function.

In step S10701, the inspection information management unit 207 causes the user to select one of the plurality of pieces of inspection information acquired from the operation unit 26 and sets the selected piece of inspection information as an inspection target. Such processing is implemented by displaying the plurality of pieces of acquired inspection information in a list format and setting of the selected piece of inspection information as the inspection target in response to the user's operation input to select one piece of inspection information from the list. Alternatively, the user may be able to directly input inspection information from the operation unit 26.

In step S10702, the control apparatus 20 transmits a signal for causing the radiation detection apparatus 10 to transition to a preparation state according to the set inspection information and thereby starts inspection.

For example, the radiation detection apparatus 10 uses a main control circuit to control a bias power source according to this signal and applies a bias voltage to a two-dimensional image pickup element. Thereafter, the control apparatus 20 uses a drive circuit to perform initialization for reading out an image signal from a pixel array to read out a dark current signal accumulated in each pixel. After the initialization, the radiation detection apparatus 10 transmits state information indicating that preparation for obtaining a radiation image is ready to the control apparatus 20. The control apparatus 20 (inspection information management unit 207) also sets an operation parameter (tube voltage or the like) of the radiation generating apparatus 30 based on the inspection information selected in step S10701. Upon receiving the notification that preparation for imaging is ready based on the state information from the radiation detection apparatus 10, the control apparatus 20 notifies the radiation generating apparatus 30 of permission for exposure to radiation.

First, in step S10703, the optical image acquisition unit 203 acquires an optical image captured by the optical imaging apparatus 40.

In step S10704, the optical image analysis unit 205 uses the optical image acquired from the optical image acquisition unit 203 and the inspection information acquired from the inspection information management unit 207 to analyze the optical image. For the optical image analysis, for example, the inference processing unit 206 (refer to FIG. 2) may perform inference processing using machine learning. As an image input to the optical image analysis unit 205, all of the images acquired by the optical image acquisition unit 203 may be used, or images to be used may be thinned out in accordance with a content of analysis and the images may be input to the optical image analysis unit 205. Details of step S10704 will be described below.

In step S10705, the control apparatus 20 acquires a result of determination performed in step S10704 and acquires information regarding notification about a detection state corresponding to the determination result. An example of correspondence between the determination result and the notification about the detection state is as illustrated in a table 10900 in FIG. 9. FIG. 9 is a table indicating correspondence between a determination result using image analysis and notification about a detection result.

In step S10706, the optical image display control unit 204 uses the optical image acquired by the optical image acquisition unit 203 and the analysis result from the optical image analysis unit 205 to control a display content, and provides the display content to the display control unit 209. The controlled display content is thereby displayed on the display unit 25. The optical image display control unit 204 arbitrarily displays the optical image and the analysis result. The optical image display control unit 204 may also perform control of the display according to a setting of the control apparatus 20 or a setting of the inspection information management unit 207. For example, the optical image display control unit 204 may display only the optical image on the display unit 25 in a case of not performing the optical image analysis.

[Optical Image Analysis Processing]

Figure 8A:
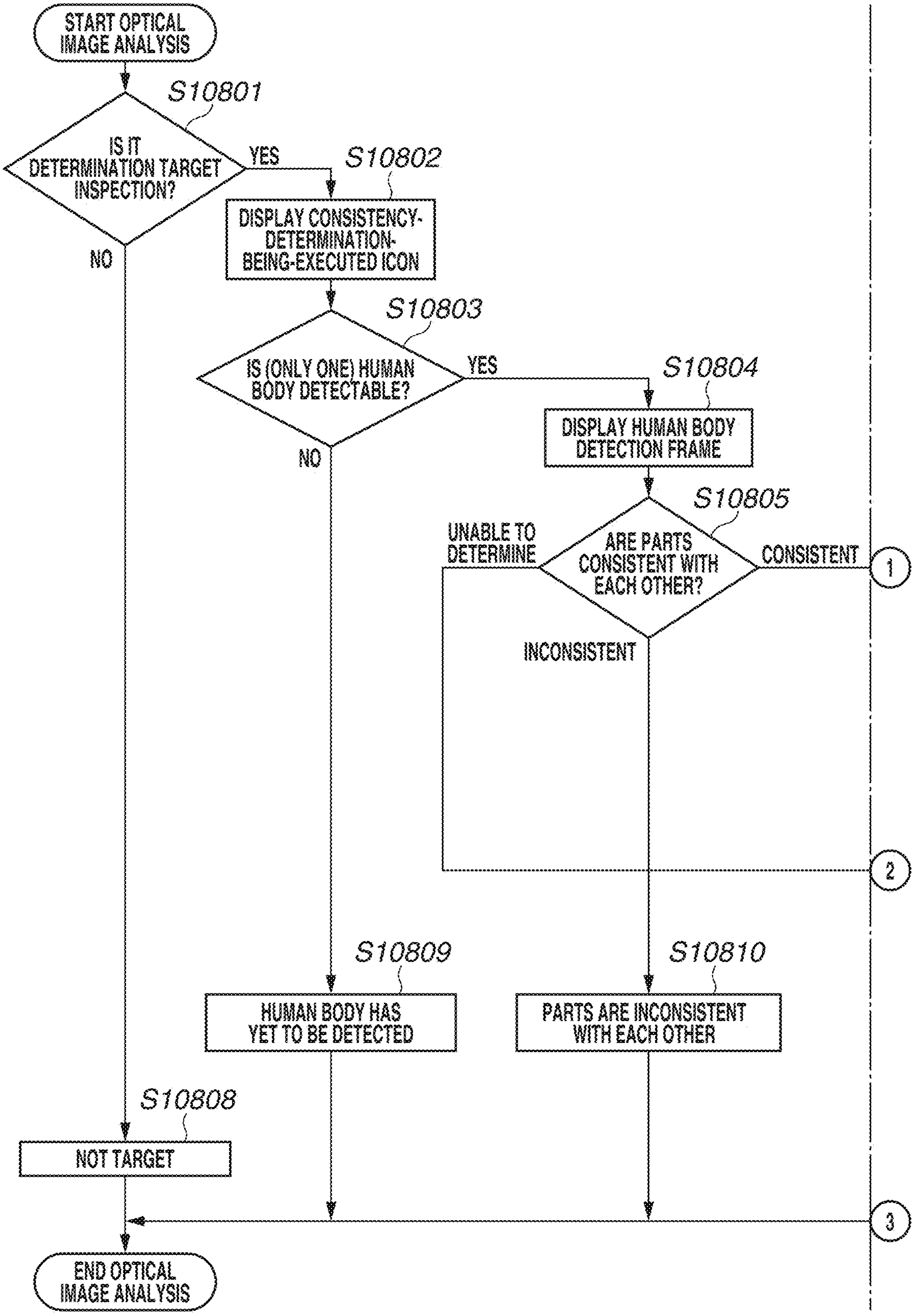
FIGS. 8A and 8B illustrate a flowchart of optical image analysis processing.
Figure 8B:
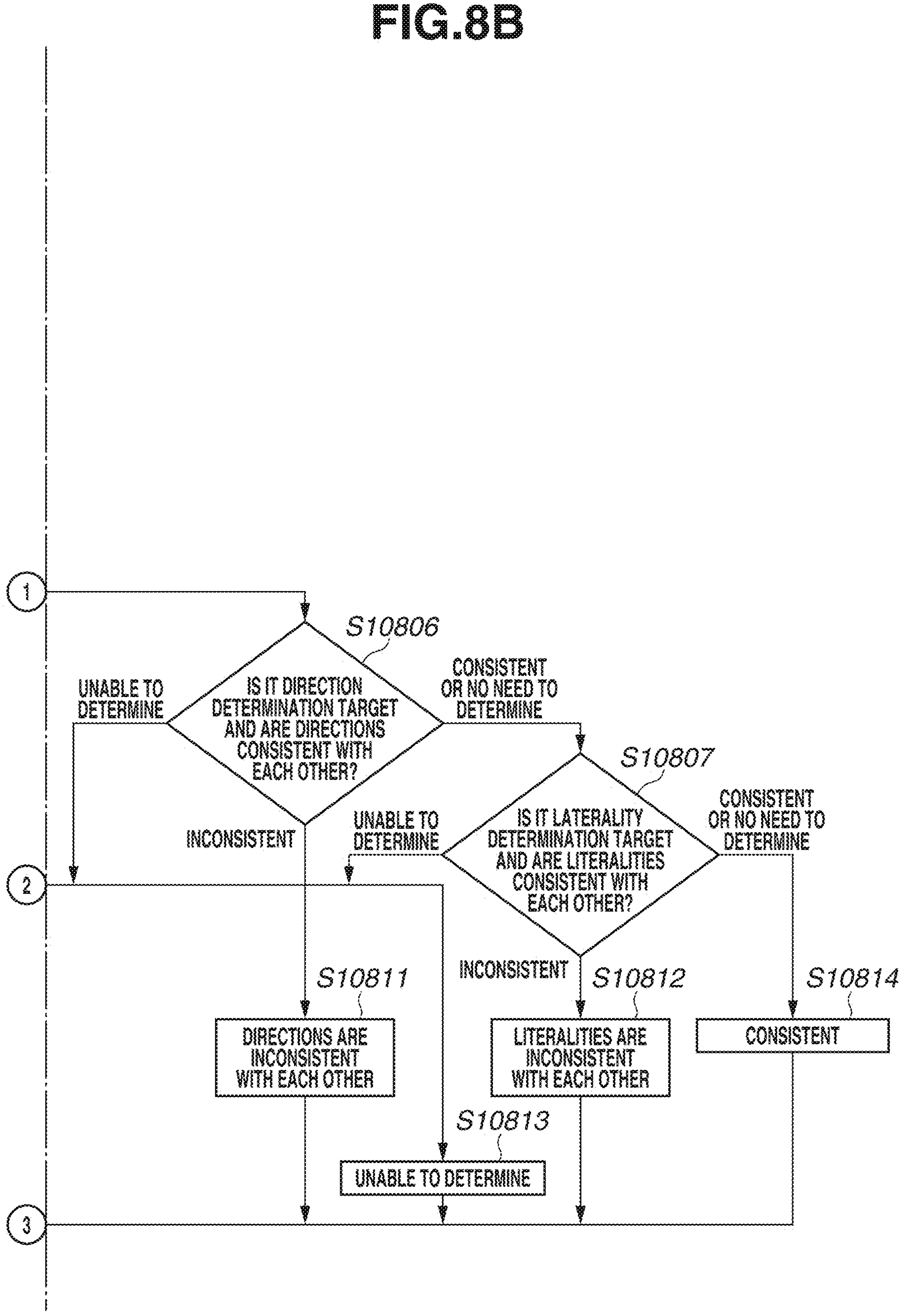

Next, optical image analysis processing (processing in step S10704) performed by the optical image analysis unit 205 will be described with reference to FIGS. 8A and 8B. FIGS. 8A and 8B are a flowchart of the optical image analysis processing. Control corresponding to this flowchart is executed by the control apparatus 20. Specifically, the control is implemented by the CPU 301 included in the control apparatus 20 loading the computer program 3031 stored in the ROM 303 or the like into the RAM 302 and operating as a corresponding function. The order of each step may be freely selected. Processing in any of steps may also not be included. Processing of storing display information may also not be performed.

In step S10801, the optical image analysis unit 205 determines whether the inspection information acquired by the inspection information management unit 207 indicates determination target inspection in optical image analysis. For example, in the optical image analysis, the optical image analysis unit 205 determines, in order to determine whether the optical image matches a content of designated analysis, that the inspection information is not a target in a case where sufficient information is not included in the inspection information. Specific examples of the above-mentioned case include, at the time of analysis intended to make determination about a part, a case where a part is not designated in the inspection information and a case where a part on which the optical image analysis unit 205 is unable to perform analysis is designated in the inspection information. In a case where the inspection information is not the target (NO in step S10801), the processing proceeds to step S10808. In step S10808, a determination result indicates that the inspection information is not the target.

In step S10802, the optical image analysis unit 205 stores display information as the determination result so as to display a consistency-determination-being-executed icon indicating the determination target inspection in the optical image analysis.

In step S10803, the optical image analysis unit 205 determines whether the optical image acquired from the optical image acquisition unit 203 includes an examinee as a target of analysis. As a method of detecting the examinee, an image recognition method using machine learning may be used. At this time, in a case where not only a patient's body serving as a subject to be imaged but also a body of a person other than the patient, such as a radiology technician who prepares for imaging, is included in the optical image, the optical image analysis unit 205 may determine that an appropriate examinee has not been successfully detecting and it is unable to detect the examinee. In a case where the optical image analysis unit 205 determines that it is unable to detect the examinee (NO in step S10803), the processing proceeds to step S10809. In step S10809, the determination result indicates that the human body has yet to be detected.

In step S10804, the optical image analysis unit 205 stores display information serving as the determination result so as to display the consistency-determination-being-executed icon indicating the determination target inspection in the optical image analysis.

In step S10805, the optical image analysis unit 205 determines whether the part in the inspection information acquired by the inspection information management unit 207 and the part serving as the optical image analysis result acquired from the optical image acquisition unit 203 are consistent with each other. Conditions for determination that the parts are consistent with each other include a case where one of the parts is included in a similar part group of the other of the parts as well as a case where the parts are strictly consistent with each other. The similar part group represents a part group that is preliminarily set for each part in consideration of an anatomical viewpoint, a human body geometric viewpoint, operations of a system, and the like. For example, a part group of arms includes upper arms, elbows, and hands. A part group of hands includes palms and fingers. The optical image analysis unit 205 performs consistency determination for the parts based on information regarding the part group. Thus, in a case where the part-to-be-imaged information obtained from the inspection information management unit 207 is an arm and the information regarding the part as the optical image analysis result obtained from the optical image acquisition unit 203 is an elbow, the optical image analysis unit 205 determines that both parts are in a similar part relationship and are consistent with each other, and notifies the display unit 25 of a result of the determination (refer to FIG. 9). In a case of this example, information regarding the part as the optical image analysis result (elbow) is included in the part-to-be-imaged information (arm) obtained from the inspection information management unit 207, and the optical image analysis unit 205 determines that both parts are similar and consistent with each other. In a case where there are different parts having an identical name, the optical image analysis unit 205 may also regard all parts in a similar part group of the parts having the identical name as the determination target. For example, in a case where the part-to-be-imaged information obtained from the inspection information management unit 207 is a finger and the information regarding the part as the optical image analysis result obtained from the optical image acquisition unit 203 is a thumb of the hand (i.e., a group of arms), the optical image analysis unit 205 may determine consistency with each of a group of toes and a group of fingers as the determination target. In this manner, in a case where there is a plurality of parts whose part-to-be-imaged information having an identical name in an imaging protocol (fingers in this example), the optical image analysis unit 205 preferably determines consistency with the part information as the image analysis result in consideration of similarity with all the parts having the identical name (all toes and all fingers in this example). Alternatively, a similar part group set in a similar part included in the similar part group may also be added to the determination target. In this case, however, it is desirable to set an upper limit on the number of additions to prevent a significant alienation from the original part. In a case where the optical image analysis unit 205 determines the part in the inspection information and the part serving as the optical image analysis result are consistent with each other because one of the parts is included in a similar part group of the other of the parts, the optical image analysis unit 205 holds the information. As a method of analyzing the part, an image recognition method using machine learning may also be used. In a case where the optical image analysis unit 205 determines that the parts are inconsistent as an analysis result (INCONSISTENT in step S10805), the processing proceeds to step S10810. In step S10810, the determination result indicates that the parts are inconsistent. In a case where the optical image analysis unit 205 fails to determine whether the parts are consistent or inconsistent and unable to make determination (UNABLE TO DETERMINE in step S10805), the processing proceeds to step S10813. In step S10813, the determination result indicates that the optical image analysis unit 205 is unable to make determination. In this manner, the optical image analysis unit 205 determines consistency between the information regarding the part estimated by the inference processing unit 206 serving as the estimation unit and the part-to-be-imaged information acquired by the inspection information management unit 207 serving as the second acquisition unit based on similarity. That is, it can also be said that, in a case where there is consistency between the information regarding the part estimated by the optical image analysis and the part-to-be-imaged information in the imaging protocol, the similarity between these pieces of information reaches an upper limit. Thus, in other words, it can also be said that the optical image analysis unit 205 determines consistency between the information regarding the part estimated by the optical image analysis and the part-to-be-imaged information in the imaging protocol in consideration of the similarity between these pieces of information.

In step S10806, the optical image analysis unit 205 also determines whether a direction in the inspection information acquired by the inspection information management unit 207 and a direction as the optical image analysis result acquired from the optical image acquisition unit 203 are consistent with each other. The determination may be omitted depending on the inspection information. In a case where the optical image analysis unit 205 determines that there is consistency using similar parts in step S10805, the determination may be omitted. As a method of analyzing a direction, an image recognition method using machine learning may be used. In a case where the optical image analysis unit 205 determines that there is inconsistency as an analysis result (INCONSISTENT in step S10806), the processing proceeds to step S10811. In step S10811, the determination result indicates that the directions are inconsistent.

In a case where the optical image analysis unit 205 fails to determine whether the directions are consistent or inconsistent and unable to make determination (UNABLE TO DETERMINE in step S10806), the processing proceeds to step S10813. In step S10813, the determination result indicates that the optical image analysis unit 205 is unable to make determination.

In step S10807, the optical image analysis unit 205 determines whether laterality in the inspection information acquired by the inspection information management unit 207 and laterality serving as the optical image analysis result acquired from the optical image acquisition unit 203 are consistent with each other. The laterality mentioned herein refers to as laterality information. While the part information is, for example, information regarding a hand, a foot, or a chest, the laterality information is four pieces of information indicating the left, the right, both the left and the right, and no laterality information. These pieces of information are referred to as L, R, B, and U as initials of Left, Right, Both and Unpaired. The determination may also be omitted depending on the inspection information. In a case where the optical image analysis unit 205 determines that there is consistency using similar parts in step S10805, the determination may also be omitted. As a method of analyzing laterality, an image recognition method using machine learning may be used. In a case where the optical image analysis unit 205 determine that there is inconsistency as the analysis result (INCONSISTENT in step S10807), the processing proceeds to step S10812. In step S10812, the determination result indicates that the lateralities are inconsistent. In a case where the optical image analysis unit 205 fails to determine whether the lateralities are consistent or inconsistent and unable to make determination (UNABLE TO DETERMINE in step S10807), the processing proceeds to step S10813. In step S10813, the determination result indicates the optical image analysis unit 205 is unable to make determination. In a case where the lateralities are consistent with each other (CONSISTENT OR NO NEED TO DETERMINE in step S10807), the processing proceeds to step S10814. In step S10814, the determination result indicates that there is consistency.

Steps S10808 to S10814 indicate states of determination results of the optical image analysis unit 205.

The optical image display control unit 204 is capable of controlling display contents of the optical image window 550 based on whether it is determined that there is consistency using similar parts in step S10805. Specifically, the optical image display control unit 204 is capable of controlling contents of notification as illustrated in the table 10900 in FIG. 9.

The notification given in the optical image analysis result 556 is not limited to a message using texts. The notification may also be given using a figure, a symbol, a color, or the like, other than texts, so as to allow each analysis result to be differentiated.

Advantageous Effects

As described in the exemplary embodiment, determining consistency between a designated imaging technique and actual registration of the examinee and notifying the user of the consistency can make the user aware of possibility of an image loss. It is thereby possible to prevent occurrence of the image loss and lead to efficiency of a workflow.

The present disclosure is not limited to the above-mentioned exemplary embodiment, and can be modified in various manners (including an organic combination of each exemplary embodiment) based on the gist of the present disclosure, and these modifications are not excluded from the scope of the present disclosure. That is, all configurations obtained by combining the above-mentioned exemplary embodiment and a modification of the exemplary embodiment are included in the present disclosure.

The present disclosure can also be implemented by installation of a program that implements one or more functions of the above-mentioned exemplary embodiment in a system or an apparatus via a network or a storage medium, and readout of the program and execution of processing of the program by one or more processors in the system or a computer of the apparatus. Furthermore, the present disclosure can also be implemented by a circuit (e.g., an application specific integrated circuit (ASIC)) that implements one or more functions.

The processor or the circuit can include a CPU, a micro processing unit (MPU), a graphics processing unit (GPU), an ASIC, and a field-programmable gate array (FPGA) circuit. The processor or the circuit can also include a digital signal processor (DSP), a data flow processor (DFP), and a neural processing unit (NPU).

The radiographing system according to the above-mentioned exemplary embodiment may be implemented as a single apparatus, or may have a configuration that communicably combines a plurality of apparatuses to execute the above-mentioned processing. Each case is included in exemplary embodiments of the present disclosure. The above-mentioned processing may be executed by a common server apparatus or a sever group. The plurality of apparatuses that constitutes the radiographing system is only required to be communicable at a predetermined communication rate, and does not necessarily exist in an identical facility or in an identical country.

The exemplary embodiments include a configuration in which a program of software that implements functions of the above-mentioned exemplary embodiment is installed in a system or an apparatus, and a computer of the system or the apparatus reads out and executes codes of the installed program.

Thus, codes of the program installed in the computer to implement the processing according to the exemplary embodiment are also one of the exemplary embodiments of the present disclosure. Alternatively, part or all of actual processing is performed by an operating system (OS) that operates on a computer based on an instruction included in the program read out by the computer, and the functions of the above-described exemplary embodiment can also be implemented by the processing.

According to the present disclosure, it is possible to support radiographic imaging based on the optical image analysis result.

OTHER EMBODIMENTS

Embodiment(s) of the present disclosure can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has been described with reference to exemplary embodiments, it is to be understood that the present disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2024-004201, filed Jan. 15, 2024, which is hereby incorporated by reference herein in its entirety.

What is claimed is:

1. A radiographing control apparatus comprising:

a first acquisition unit configured to acquire an optical image regarding a subject;

an estimation unit configured to estimate information regarding a part of the subject from the optical image;

a second acquisition unit configured to acquire part to be imaged information in an imaging protocol regarding the subject; and a determination unit configured to determine whether there is consistency between the information regarding the part estimated by the estimation unit and the part to be imaged information acquired by the second acquisition unit based on similarity.

2. The radiographing control apparatus according to claim 1, wherein, in a case where one of the information regarding the part and the part to be imaged information is included in the other of the information regarding the part and the part to be imaged information, the determination unit is configured to determine that there is consistency between the information regarding the part and the part to be imaged information.

3. The radiographing control apparatus according to claim 1, wherein, in a case where there is a plurality of pieces of information regarding parts having an identical name, the information being one of the information regarding the part or the part to be imaged information, the determination unit is configured to determine the consistency based on similarity of the other of the information regarding the part or the part to be imaged information with all of the parts having the identical name.

4. The radiographing control apparatus according to claim 1, wherein the information regarding the part is information regarding a direction of the part.

5. The radiographing control apparatus according to claim 1, wherein the information regarding the part is information regarding laterality of the part.

6. A radiographing system, comprising:

a radiation detection apparatus configured to generate a radiation image by being irradiated with radiation; and a radiographing control apparatus including a first acquisition unit configured to acquire an optical image regarding a subject, an estimation unit configured to estimate information regarding a part of the subject from the optical image, a second acquisition unit configured to acquire part to be imaged information in an imaging protocol regarding the subject, and a determination unit configured to determine whether there is consistency between the information regarding the part estimated by the estimation unit and the part to be imaged information acquired by the second acquisition unit based on similarity.

7. The radiographing system according to claim 6, further comprising a notification unit configured to give notification about a result of determination performed by the determination unit.

8. The radiographing system according to claim 7, wherein the notification unit is configured to change a content of the notification in accordance with similarity between the information regarding the part and the part to be imaged information.

* * * * *